United States Patent [19]

McConnell et al.

[11] 4,234,730
[45] Nov. 18, 1980

[54] PROCESS OF PREPARING SELECTIVE MIXTURES OF PIPERAZINE AND ETHYLENEDIAMINE

[75] Inventors: Thomas T. McConnell; Thomas H. Cour, both of Austin, Tex.

[73] Assignee: Texaco Development Corp., White Plains, N.Y.

[21] Appl. No.: 78,117

[22] Filed: Sep. 24, 1979

[51] Int. Cl.³ .......................................... C07D 295/02
[52] U.S. Cl. .................................... 544/358; 564/511
[58] Field of Search .................... 544/358; 260/583 P

[56] References Cited

U.S. PATENT DOCUMENTS 3,037,023  5/1962  Moss et al. .......................... 544/358

Primary Examiner—Jose Tovar
Attorney, Agent, or Firm—Carl G. Ries; Robert A. Kulason; James L. Bailey

[57] ABSTRACT

Covers a process for preparing a mixture of piperazine and ethylenediamine by the hydrogenation reaction of monoethanolamine and ammonia utilizing a nickel-copper-chromium catalyst. The improvement of the invention involves predetermining the ratio of ethylenediamine to piperazine in the product mix by varying the hydrogen feed rate. Increasing said feed rate causes said ratio to decrease.

3 Claims, No Drawings

PROCESS OF PREPARING SELECTIVE MIXTURES OF PIPERAZINE AND ETHYLENEDIAMINE

BACKGROUND OF THE INVENTION

1. Field of the Invention

This invention relates to a process of making selective mixtures of piperazine and ethylenediamine by reacting monoethanolamine and ammonia in presence of hydrogen and a nickel-copper-chromium catalyst.

2. Description of the Prior Art

U.S. Pat. No. 3,037,023 describes the production of piperazine by means of reacting monoethanolamine and ammonia in presence of hydrogen, utilizing a variety of conventional hydrogenation catalysts. One particular catalyst of this type which may be used in the reaction is disclosed in U.S. Pat. No. 3,152,998 which may be based on nickel-copper-chromium.

In the above reaction normally the two major products are produced. The market demand for the individual components of the mixture of piperazine and ethylenediamine is constantly changing. It would therefore be a distinct advantage in the art if a method were devised whereby one could cause a predominance of one of the components of the mixture by somehow adjusting one or more process conditions.

It therefore becomes an object in the invention to provide a method of adjusting the ratio of ethylenediamine to piperazine in the mixture of these products so produced by reacting monoethanolamine and ammonia in presence of hydrogen. Other objects will appear hereinafter.

SUMMARY OF THE INVENTION

In accordance with the invention, a method of preparing selective mixtures of piperazine and ethylenediamine has been devised whereby the predominance of one over the other can be adjusted. Essentially, this is effected by reacting monoethanolamine and ammonia in presence of hydrogen and a nickel-copper-chromium catalyst, and in adjusting the ratio of ethylenediamine to piperazine in the product mix by varying the hydrogen feed rate such that by increasing said feed rate said ratio is decreased.

DETAILED DESCRIPTION OF THE PREFERRED EMBODIMENTS

In more detail, the present invention essentially involves a process for varying the ratio of ethylenediamine to piperazine in such product mix derived from the reaction of monoethanolamine with ammonia in presence of hydrogen. Essentially, said ratio is proportional in an inverse manner to the amount of hydrogen utilized in said reaction in terms of a hydrogen rate. The process carried out here is run in the conventional manner, particularly as set out on U.S. Pat. No. 3,037,023. However, it was surprisingly discovered that one could increase the amount of piperazine in terms of its ratio to ethylenediamine by increasing the rate of hydrogen utilized per pound of monoethanolamine converted. Thus, by increasing the hydrogen rate, usually expressed in standard cubic feet of hydrogen per pound of monoethanolamine charged, one could increase the amount of piperazine, with correspondingly a decrease in ethylenediamine noted. Heretofore, the art was not aware of such a relationship.

As a typical guideline the weight ratio of ethylenediamine to piperazine at a monoethanolamine conversion ranging from about 30 to about 70 percent at a hydrogen rate of about 0.1 to about 1.5 standard cubic feet of hydrogen per pound of monoethanolamine will range from about 5 up to about 12 or greater to 1. On the other hand, at a hydrogen rate of about 3 standard cubic feet per pound of monoethanolamine up to about 9 the ethylenediamine to piperazine ratio will usually fall within the range of from about 1.2 to about 4 to 1, depending upon the amount of monoethanolamine conversion taking place. In any event as hydrogen rate is increased the ratio of ethylenediamine to piperazine (EDA/Pip) proportionately decreases in a straight line fashion.

The catalyst used here is a nickel-copper-chromium hydrogenation catalyst of the type set out in U.S. Pat. No. 3,152,998. Usually the catalyst consists of about 5-80 percent nickel, about 10 percent to about 49 percent copper, and 1 percent to about 10 percent chromium, based upon the weight of the metals only. The metals are usually in oxide form, and the catalyst is usually contained on a support such as in pellet form. The support or carrier used may be any one of inert to process conditions such as refractory support, charcoal, silica, alumina and the like which are capable of being employed with the active catalyst. The methods of preparing such a catalyst on supports are wellknown in the art.

The reaction itself may be carried out over a wide range of conditions. Typically, the reaction if carried out at a temperature within the range of from about 100° C. to about 400° C., and more often at a temperature of 150°-250° C. The pressure employed usually ranges from about 30 to about 400 atmospheres, and is preferably 65-225 atmospheres.

The amount of ammonia employed is usually 2-20 moles per mole of monoethanolamine. Preferably 4-10 moles of ammonia are employed per mole of monoethanolamine.

The particular space velocity of the reaction (grams monoethanolamine/hour/cc catalyst) is not critical in the process. However, we prefer to conduct the reaction at a velocity of between about 0.5 to about 10 grams total liquid feed/hour/cc catalyst.

The reaction here can be performed in either a batch or continuous manner, with the latter being preferred. Further, suitable reactors include either a closed autoclave resulting in a batch process, or a tubular reactor which can be operated in a continuous manner.

The desired individual products of piperazine and ethylenediamine can then be recovered from the reaction media by any techique known in the art, such as by distillation, etc.

This invention will be further illustrated by the following examples which are intended to be illustrative and are not to be construed to place limitations on the scope of this invention.

EXAMPLE I

Here monoethanolamine was fed to a tubular reactor containing two gallons of a nickel-copper-chromium oxide catalyst. The liquid feed to the reactor contained six mols of ammonia per mol of monoethanolamine. The reactor space velocity was approximately 4.5 grams of liquid per hour per ml. catalyst vol. at a pressure of 2500 psig.

In this series of runs the hydrogen feed rate was varied, and as can be seen from Table I below the EDA/-

Pip weight ratio inversely varied with hydrogen rate while maintaining the monoethanolamine (MEA) conversion at an approximate 60% figure. Results are given below in Table I.

TABLE I

| Run | H$_2$Rate SCFH$_2$/lb. MEA | MEA Conversion | EDA/Pip Wt. Ratio |
|-----|---------------------------|----------------|-------------------|
| 1   | 0.14                      | 63.8           | 6.0               |
| 2   | 1.03                      | 60.2           | 3.7               |
| 3   | 3.87                      | 60.6           | 2.2               |
| 4   | 8.17                      | 66.5           | 1.3               |

EXAMPLE II

Using the same reactor conditions as in Example I the following results were obtained at approximately 50% MEA conversion.

| Run | H$_2$Rate SCFH$_2$/lb. MEA | MEA Conversion | EDA/Pip Wt. Ratio |
|-----|---------------------------|----------------|-------------------|
| 1   | 0.15                      | 56.2           | 6.9               |
| 2   | 1.1                       | 48.4           | 4.4               |
| 3   | 1.8                       | 53.2           | 4.3               |
| 4   | 4.1                       | 55.1           | 2.4               |
| 5   | 8.3                       | 50.3           | 1.8               |

EXAMPLE III

Using the same reactor conditions as in Example I the following results were obtained at approximately 35% MEA conversion.

| Run | H$_2$Rate SCFH$_2$/lb. MEA | MEA Conversion | EDA/Pip Wt. Ratio |
|-----|---------------------------|----------------|-------------------|
| 1   | 0.17                      | 36.1           | 11.0              |
| 2   | 2.0                       | 35.7           | 4.5               |
| 3   | 4.4                       | 35.4           | 3.6               |
| 4   | 8.4                       | 31.8           | 3.0               |

From the foregoing description examples of this invention, those of ordinary skill in the art may make many modifications and variations therefrom without departing from the scope of the invention as hereinafter claimed.

We claim:

1. In a process of preparing a mixture of piperazine and ethylenediamine by reacting monoethanolamine and ammonia in presence of hydrogen and a nickel-copper-chromium catalyst; the improvement which comprises adjusting the ratio of ethylenediamine to piperazine in said product mixture by varying the hydrogen feed rate such that by increasing said feed rate said ratio is decreased.

2. The process of claim 1 which is carried out at a pressure of 30–400 atmospheres and a temperature of 100°–400° C.

3. The process of claim 1 wherein said catalyst comprises nickel, copper and chromium metal oxides having about 50 percent to about 80 percent nickel, about 10 percent to about 49 percent copper, and about 1 percent to about 10 percent chromium, based on the total weight of said metals.

* * * * *